US008231629B2

(12) United States Patent
Lerner et al.

(10) Patent No.: US 8,231,629 B2
(45) Date of Patent: Jul. 31, 2012

(54) SYSTEM AND METHOD FOR LOCATING OF DISTAL HOLES OF AN INTRAMEDULLARY NAIL

(75) Inventors: Alexander Lerner, Karmiel (IL); Alexander Nassonov, Kiryat Shmona (IL); Lev Diamant, Korazim (IL)

(73) Assignee: L.R.S. Ortho Ltd., Katzrin (IL)

( * ) Notice: Subject to any disclaimer, the term of this patent is extended or adjusted under 35 U.S.C. 154(b) by 574 days.

(21) Appl. No.: 12/308,877

(22) PCT Filed: Jul. 1, 2007

(86) PCT No.: PCT/IL2007/000809
§ 371 (c)(1),
(2), (4) Date: Mar. 25, 2009

(87) PCT Pub. No.: WO2008/001386
PCT Pub. Date: Jan. 3, 2008

(65) Prior Publication Data
US 2009/0306665 A1     Dec. 10, 2009

Related U.S. Application Data

(60) Provisional application No. 60/817,102, filed on Jun. 29, 2006.

(51) Int. Cl.
*A61B 17/17*     (2006.01)
*A61B 17/88*     (2006.01)
(52) U.S. Cl. .............................. 606/87; 606/96; 606/97
(58) Field of Classification Search ............. 606/62–68, 606/96–98, 86 R, 87
See application file for complete search history.

(56) References Cited

U.S. PATENT DOCUMENTS

| 4,667,664 | A | * | 5/1987 | Taylor et al. ................. 606/64 |
| 4,803,976 | A | | 2/1989 | Frigg et al. |
| 4,848,327 | A | * | 7/1989 | Perdue ........................... 606/54 |
| 4,865,025 | A | * | 9/1989 | Buzzi et al. ..................... 606/96 |
| 4,881,535 | A | * | 11/1989 | Sohngen ........................ 606/98 |
| 5,031,203 | A | * | 7/1991 | Trecha ......................... 378/205 |
| 5,281,224 | A | * | 1/1994 | Faccioli et al. ................. 606/62 |
| 5,411,503 | A | | 5/1995 | Hollstien et al. |
| 5,417,688 | A | * | 5/1995 | Elstrom et al. ................. 606/64 |
| 5,433,720 | A | * | 7/1995 | Faccioli et al. ................. 606/87 |
| 5,478,343 | A | | 12/1995 | Ritter |

(Continued)

FOREIGN PATENT DOCUMENTS

DE     43 44 470 A1     6/1995

(Continued)

*Primary Examiner* — Thomas Barrett
*Assistant Examiner* — Zade Coley
(74) *Attorney, Agent, or Firm* — The Nath Law Group; Joshua B. Goldberg; Jerald L. Meyer

(57) ABSTRACT

The present invention relates to alignment systems and methods for detecting a distal hole of an intramedullary nail. A jig is attached to the proximal end of the nail and also mounted on the bone. The jig has an adjustable positioning head that includes a drill axis hole along with an alignment pin. The alignment pin includes reference marks that are visible in X-ray images and helps to align the positioning head drill axis with the distal hole of the intramedullary nail. A light source is insertable into the nail in order to shine light out of the distal hole to illuminate a spot on the bone surface as an alignment aid. Viewing optics are mountable on the positioning head for viewing the illuminated spot created by the light source in the intramedullary nail.

10 Claims, 7 Drawing Sheets

U.S. PATENT DOCUMENTS

| | | | |
|---|---|---|---|
| 5,540,691 A * | 7/1996 | Elstrom et al. | 606/64 |
| 5,584,838 A * | 12/1996 | Rona et al. | 606/96 |
| 6,027,506 A | 2/2000 | Faccioli et al. | |
| 6,039,742 A | 3/2000 | Krettek et al. | |
| 6,129,729 A | 10/2000 | Snyder | |
| 6,635,061 B1 | 10/2003 | Snyder | |
| 6,656,189 B1 * | 12/2003 | Wilson et al. | 606/97 |
| 6,702,823 B2 * | 3/2004 | Iaia | 606/98 |
| 6,718,194 B2 * | 4/2004 | Kienzle, III | 600/424 |
| 7,029,478 B2 * | 4/2006 | Hollstien et al. | 606/96 |
| 7,481,815 B2 * | 1/2009 | Fernandez | 606/97 |
| 7,887,545 B2 * | 2/2011 | Fernandez et al. | 606/97 |
| 2006/0098851 A1 | 5/2006 | Shoham et al. | |
| 2008/0075348 A1 | 3/2008 | Rappaport et al. | |

FOREIGN PATENT DOCUMENTS

| | | |
|---|---|---|
| WO | WO 01/89395 A2 | 11/2001 |
| WO | WO 03/043485 A2 | 5/2003 |
| WO | WO 03/105659 A2 | 12/2003 |
| WO | WO 2004/069063 A1 | 8/2004 |
| WO | WO 2008/001386 A2 | 1/2008 |

* cited by examiner

SYSTEM AND METHOD FOR LOCATING OF DISTAL HOLES OF AN INTRAMEDULLARY NAIL

CROSS-REFERENCE

This is a National Phase Application filed under 35 U.S.C. 371 of International Application No. PCT/IL2007/000809, filed Jul. 1, 2007, claiming the benefit under 35 USC 119(e) of U.S. Provisional Application No. 60/817,102, filed Jun. 29, 2006, the entire contents of each of which is hereby incorporated herein by reference in its entirety.

FIELD OF THE INVENTION

This invention relates to systems and methods of detecting a location of distal holes of an intramedullary nail implanted into of a bone.

BACKGROUND OF THE INVENTION

For the surgical repair and stabilization of fractures of long bones, such as femur, tibia, humerus and fibula, it has long been known in medical practice to insert an intramedullary nail, which is a tubular metal part, of appropriate length into the interior portion of the bone. The nail usually has a pair of transverse holes adjacent to its proximal end (proximal holes) and a pair of transverse holes adjacent to its distal end (distal holes). In order to enhance the healing of the bone, the nail must provide a rigid structure about which the broken portions of the bone may adhere. Thus, the nail must be secured with respect to the bone. The securing of the nail is achieved by means of transversely extending screws or bolts which are screwed into the bone and pass through the surrounding tissue and through the transverse holes.

The procedure for inserting the screws requires: (a) accurate location of the transverse holes in the nail; (b) drilling screw holes in precise alignment with the transverse holes and preventing the drill from touching the nail; (c) inserting the screws into the drilled holes and through the transverse holes so as to secure the nail with respect to the bone.

The problem has always been that once the nail is inserted into the bone, the transverse holes are said to be "blind" in the terms of the bone-drilling alignment that must be achieved. Therefore, the most critical part of this procedure is to determine from outside the location, particularly the center, and the axis of these holes.

For this purpose, it is known to use a jig including a frame and different positioning means, by means of which approximate locations of the holes are determined before the nail is inserted into the bone. For proximal holes the problem is solved by means of such a jig relatively simply, since the proximal holes are adjacent to the area of the attachment of the frame of the jig and their location with respect to the proximal end of the nail almost doesn't differ from the location determined before the nail was inserted into the bone.

The determination of the location of the distal holes is much more difficult, due to the fact that the nail may have undergone a slight bent or twisting during the insertion thereof into the bone, so that the distal holes no longer have the same location with respect to the proximal end of the nail, as it was prior to its insertion.

Due to the above mentions limitations, majority of techniques have to rely on X-rays for assurance of the alignment. C-arm is often used for this purpose, since it allows directional control of the X-ray beam. One of the most common techniques using C-arm is a so-called "free hand technique". This technique depends heavily on the experience and steady hand of the surgeon. Moreover, the technique involves a great radiation exposure of the surgeon while working with hands close to the X-ray beam.

Several approaches have been used to determine the location of the transverse holes. U.S. Pat. Nos. 4,803,976; 5,411,503; 6,129,729; 6,635,061 and 6,656,189 disclose examples of different sighting and aiming jigs. U.S. Pat. No. 5,433,720 have proposed magnetic detection for location of a central axis of the holes. U.S. Pat. Nos. 4,865,025; 6,207,506 and 6,039,742 disclose several methods for locating the holes using all-mechanical devices. WO 03/105659 discloses a robot guided system comprising a miniature robot holding a targeting drill guide, which is automatically positioned by the robot relative to the distal holes. Finally, U.S. Pat. Nos. 5,540,691 and 5,417,688 disclose an optical system and method for locating the distal holes using a light source positioned adjacent to the holes.

SUMMARY OF THE INVENTION

According to one aspect of the present invention there is provided a system for use with a hollow intramedullary nail having a proximal end, a distal end and at least one distal hole formed in the nail's wall adjacent said distal end and having a hole axis, for detecting a location of said distal hole when the nail is implanted into a intramedullary canal of a bone, the system comprising:

- a jig adapted for being mounted on said nail so as to constitute a bridge between the proximal end of said nail and a distal end of said bone, and having a positioning head with a guiding axis oriented generally perpendicular to the nail's longitudinal axis, adapted for receiving therein at least a drill bit so that the drill bit's axis is aligned with said guiding axis, the positioning head being adapted to bring said guiding axis into different spatial positions with respect to said hole axis;
- a disposable member insertable into said nail and having a nail light source for emitting light along said distal hole axis so as to create an illuminated spot on an outer surface of said bone, said nail light source is of a kind providing collimated light and, said member further comprises means for positioning an axis of a collimated beam created by said light along said hole axis; and
- viewing optics mountable in said positioning head along said guiding axis for viewing said illuminated spot.

The viewing optics, such as aiming telescope, may allow viewing the illuminated spot by eye, or it may comprise an imaging camera for providing an image thereof e.g. on a display.

The positioning head may further comprise a passage extending along and coaxial with said guiding axis for receiving therein a variety of members such as for example the viewing optics, the alignment pin, a drilling guide for the drilling bit and different kinds of trocars.

The system further comprises an alignment pin having a pin proximal end, a pin distal end, a pin axis, and adapted for mounting in said passage so that said pin axis is aligned with said guiding axis and so that the pin distal end faces towards the bone. The alignment pin may further comprise a collimated light source, such as laser pointer, disposed at its proximal end for projecting an alignment beam along said guiding axis in the direction away from the alignment pin, and reference marks on its outer surface visible in X-ray images. The marks are disposed on the outer surface of the pin coaxial with the pin axis at predetermined locations therealong and have predetermined radial dimensions. The marks may be in the form of rings or other suitable form.

The jig may further comprise various support portions for affixing thereof to the bone and to the nail. These portions may be disposed at any location on the jig. In addition, the jig may comprise a guiding joint and screws for rough and fine adjustment of the positioning head with respect to the distal hole axis.

The system may further comprise, or may be adapted for use with, an X-ray machine, such as C-arm allowing taking X-ray images of the bone with the nail and the jig attached to it, from different angular positions. The X-ray images may provide information such as relative disposition of the alignment pin with respect to the distal hole axis and circularity of the distal holes. The C-arm may further comprise a mirror attached to its receiver or its source, which, together with the laser pointer of the alignment pin, allow a precise alignment of the C-arm's axis with the alignment pin axis and consequently the distal hole axis.

According to another aspect of the present invention there is provided a method for detecting a location of at least one distal hole of a hollow intramedullary nail implanted into a intramedullary canal of a bone, having a proximal end, a distal end and at least one distal hole formed in the nail's wall adjacent said distal end and having a hole axis that is, by means of a system as previously described with respect to the first aspect of the present invention. The method comprises:
(a) fixating said jig to the proximal end of the nail and the distal end of the bone;
(b) inserting the viewing optics into said positioning head;
(c) inserting the disposable member into said nail and activating said nail light source to emit light along said distal hole axis so as to create an illuminated spot on an outer surface of said bone;
(d) viewing said illuminated spot and determining location of its center; and
(e) using the determined location of the center of said illuminated spot for determining the location of the intersection of the distal hole axis with the outer surface of the bone.

The method may further comprise providing the alignment pin described above, replacing the viewing optics with the alignment pin and positioning the distal end of said pin at the center of the illuminated spot on the outer surface of the bone, so as to indicate an entry point for further future entry thereat of the drilling bit.

According to another embodiment of the present invention, the method may further comprise taking X-ray images of the nail and the alignment pin. The X-ray images are taken from at least two different angles using the C-arm, which is adjusted as previously described.

The method may comprise one or both of the following stages:
Pre-adjustment of the positioning head prior to the insertion of the nail into the bone; and
Initial adjustment of the C-Arm and calculation of the parameters of initial position of the guiding axis of the system relative to the hole axis.

The method provides a precise alignment of the positioning head axis and the hole axis, so that when the drill bit is inserted therein after the adjustment is completed is aligned with the hole axis and precise drilling of holes through the bone may be achieved. In addition, the number of X-ray images needed to be taken is relatively small, e.g. it may be sufficient to only take from two to four images, which prevents unnecessary radiation of the patient and the medical stuff.

According to another aspect of the present invention there is provided a system for use with a hollow intramedullary nail having a proximal end, a distal end and at least one distal hole formed in the nail's wall adjacent said distal end and having a hole axis, for detecting a location of said distal hole when the nail is implanted into a intramedullary canal of a bone, the system comprising:
a jig adapted for being mounted on said bone so as to constitute a bridge between the proximal end of said nail and a distal end of said bone, and having a positioning head with a ball joint, said ball joint having a guiding axis oriented generally perpendicular to the nail, adapted for receiving therein at least a drill bit so that the drill bit's axis is aligned with said guiding axis, the positioning head being movable to bring said guiding axis into different spatial positions with respect to said hole axis; and
an alignment pin having a pin proximal end, a pin distal end, and a pin axis, and being adapted for mounting in said ball joint so that said pin axis is aligned with said guiding axis and so that the pin distal end faces towards the bone, wherein the pin further comprises reference marks on its outer surface, visible in X-ray images.

According to yet another aspect of the present invention there is provided a method for detecting a location of at least one distal holes of hollow intramedullary nail, that is implanted into a intramedullary canal of a bone, having a proximal end, a distal end and at least one distal hole formed in the nail's wall adjacent said distal end and having a hole axis, by means of a system the previous aspect. The method comprises:
fixating said jig to the proximal end of the nail and the distal end of the bone;
inserting the alignment pin into said ball joint so that said pin axis is aligned with said guiding axis and so that the pin distal end faces towards the bone;
determining a location of a projection of said hole axis on the outer surface of the bone;
positioning the distal end of said pin at said location on the outer surface of the bone; and
determining the location of said distal hole axis by calculating distances and angles desired for aligning the pin axis with the hole axis taking into account parameters of the reference marks in X-ray images;
Determining the location of a projection of the hole axis on the outer surface of the bone may be achieved by such means as viewing optics previously described, or any other suitable means.

The system and method according to the latter aspects of the present invention may further comprise any features of the system and method according to the former aspects of the present invention.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
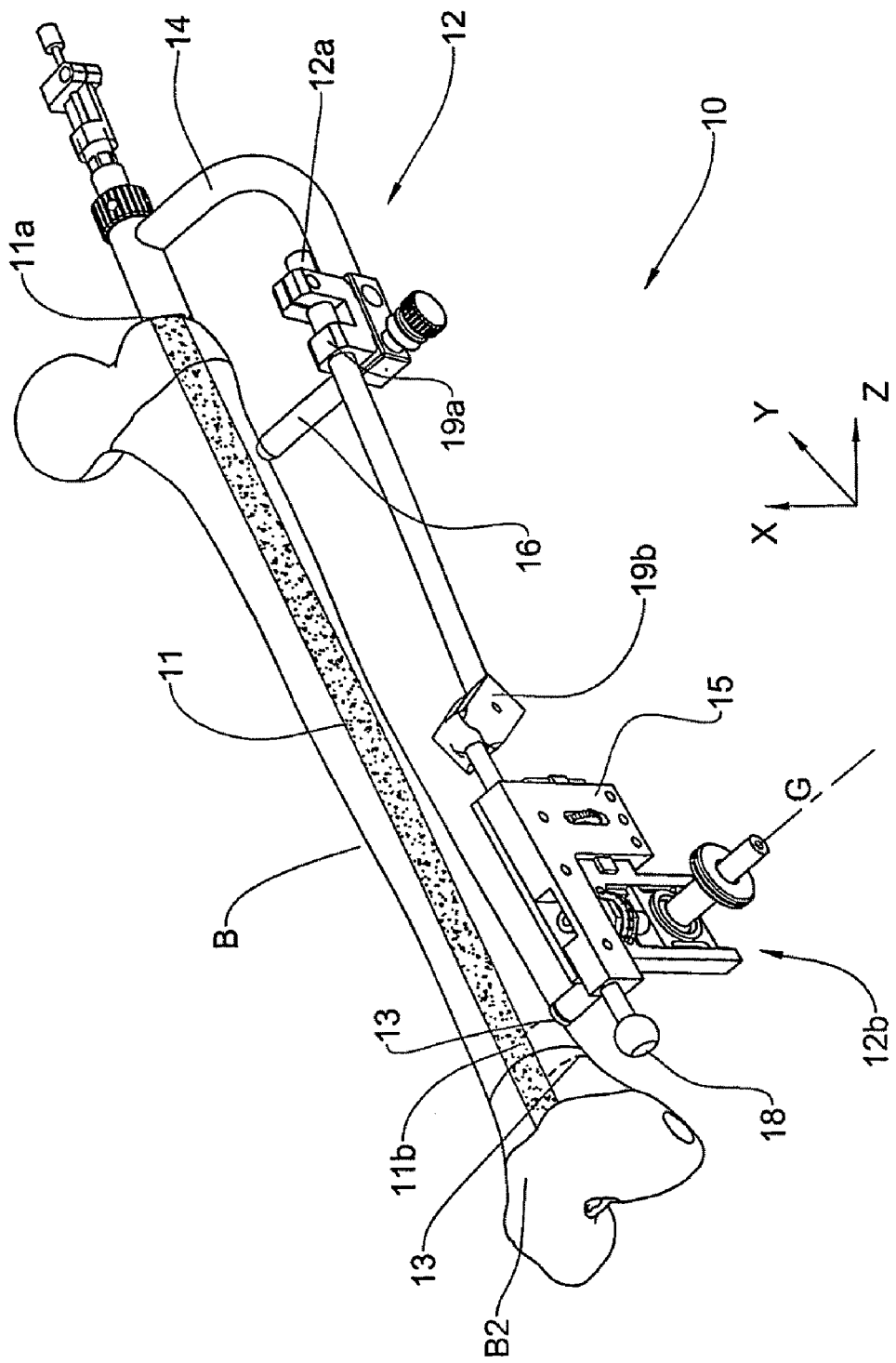
FIG. 1A is schematic perspective view of a system according to one embodiment of the present invention, including a nail inserted within a bone.
Figure 1B:
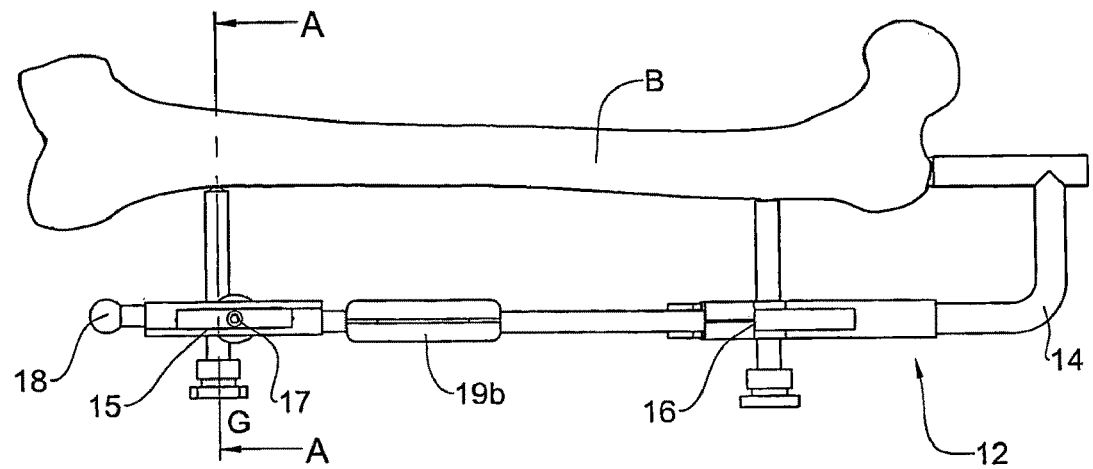
FIG. 1B is schematic plan view of the system shown in FIG. 1A.
Figure 2:
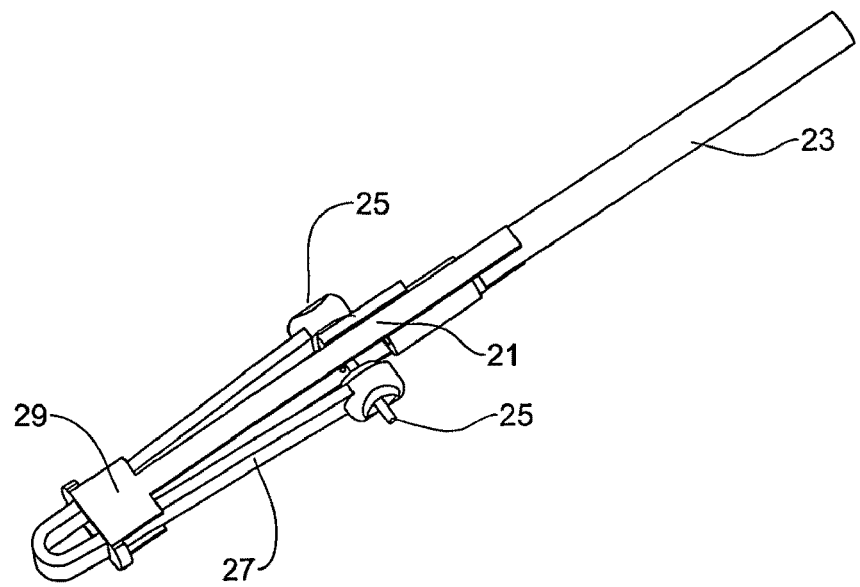
FIG. 2 is a schematic illustration of a disposable member constituting a part of the system shown in FIG. 1.

FIGS. 1A, 1B and 2 schematically illustrate a system 10 for use with a hollow intramedullary nail 11 when implanted into a intramedullary canal of a bone B. The nail has a proximal end 11a, a distal end 11b and two transverse distal holes 13 formed in the nail walls adjacent the distal end 11b, each having hole axis H (not shown), and is designed for determining the location of the holes 13.

The system 10 comprises a first member in the form of a jig 12 (FIGS. 1A and 2) adapted for use externally relative to the bone B, and a disposable member 22 (FIG. 2), adapted for insertion in the nail 11, when inserted in the bone B.

The jig 12 has a jig proximal end 12a and a jig distal end 12b, and it comprises a proximal support portion 16 and a distal support portion 18, respectively. The jig 12 is adapted to be attached at its proximal end to the proximal end 11a of the nail 11 by a handle 14, with both the proximal and distal support portions 16 and 18 being attached to the bone, as shown. Adjacent to its distal end 12b, the jig 12 further comprises a positioning head 15 with a ball joint 17 (FIG. 1B) having a passage 17a extending along and co-axial with a guiding axis G oriented generally perpendicular to the nail 11. The jig 12 further comprises guiding joints and screws as follows: a proximal joint 19a which is adjacent to the proximal support portion 16, a universal joint 19b, which is positioned between the proximal end 12a of the jig 12 and the positioning head 15, and positioning screws 15a and 15b (not shown), which are part of the positioning head 15. The positioning screws 15a and 15d allow the ball joint 17 to move in any of the X or Y directions (shown by arrows in FIG. 1A) so as to bring its guiding axis G into different spatial positions with respect to the hole axis H and to the positioning head 15.

In operation, the jig 12 together with the handle 14 creates a rigid bridge between a distal end B2 of the bone B and the proximal end 11a of the nail 11, which facilitates a procedure of positioning of the positioning head 15 and then drilling of the holes, by the limitation of mutual movement of the nail 11 with respect to the bone B. The proximal support portion 16 and the distal support portion 18 (shown only partly) of the jig 12 contribute to the stability of the created bridge.

The second disposable member 22 of the system 10 has a laser source 21, a stem (laser stick) 23, two locking bosses 25, a spring 27 and an unlocking frame 29. This disposable member is designed in a way that allows the member 22 with it's locking bosses 25 to be disposed exactly at the distal hole 13 axis and to allow either locking the laser source 21 inside the nail having the laser beam directed through the opening in the center of the locking boss 25, or unlocking the stem 23 with the laser source 21 from the bosses 25 at the end of the initial pre-adjustment of the system. The laser source 21 may be of any appropriate type and it may emit radiation of a wavelength of 550 nm to 2.2 μm.

Figure 3:
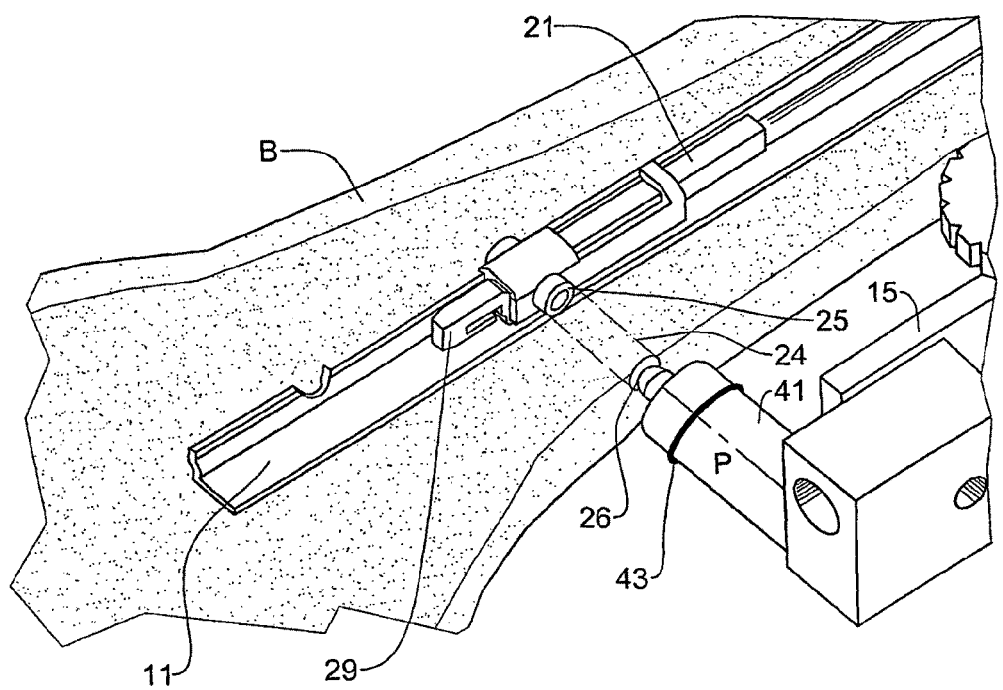
FIG. 3 is a schematic illustration of the disposable member shown in FIG. 2, when inserted within the nail seen in FIG. 1.

As shown in FIG. 3, in operation, the disposable member 22 is inserted into the nail 11 so that a laser beam 24, emitted by the laser source 21, projects through the distal hole 13 of the nail 11 and is coaxial with its axis H, thereby creating an illuminated spot 26 on the outer surface of the bone B.

Figure 4:
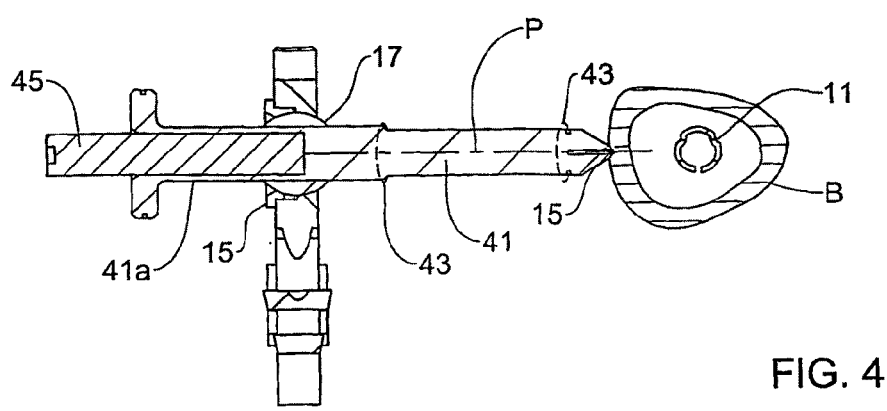
FIG. 4 is a schematic cross-sectional view of the system shown in FIGS. 1A and 1B, taken along the line A-A in FIG. 1B.

With reference to FIGS. 3 and 4, the system also comprises an alignment pin 41 receivable within the passage 17a of the ball joint 17 within the positioning head 15. As shown in FIG. 4, the alignment pin 41 has a proximal end 41a, a distal and 41b and a pin axis P. The alignment pin 41 comprises reference marks 43 on its outer surface, which are visible in X-ray images. The alignment pin 41 may further comprise a laser pointer 45 at its proximal end 41a.

Figure 8A:
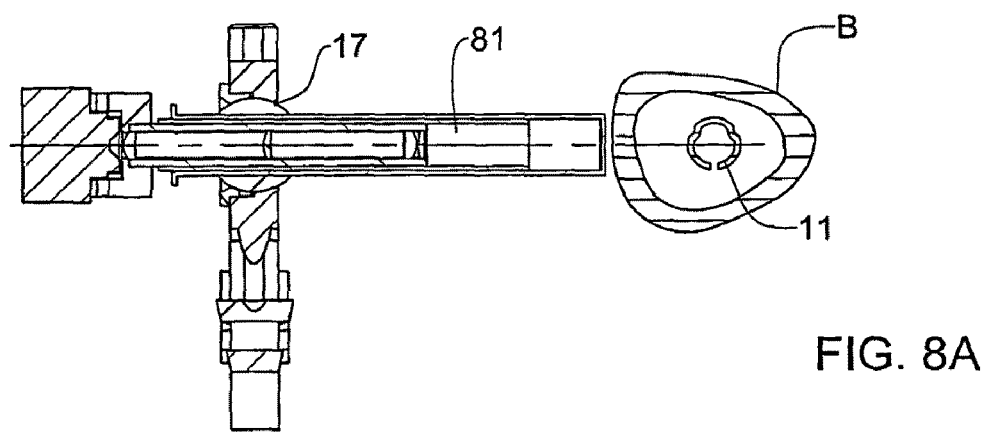
FIGS. 8A and 8B are illustrations of the system shown in FIG. 4, where an alignment pin is replaced with a viewing optics and a drill guide, respectively.

The system may further comprise a viewing optics 81, such as aiming telescope with a TV camera, shown in FIG. 8A, and a penetrating trocar (not shown), both receivable within the 17a of the ball joint 17 of the positioning head 15, whose use will be further described in more detail.

Figure 5:
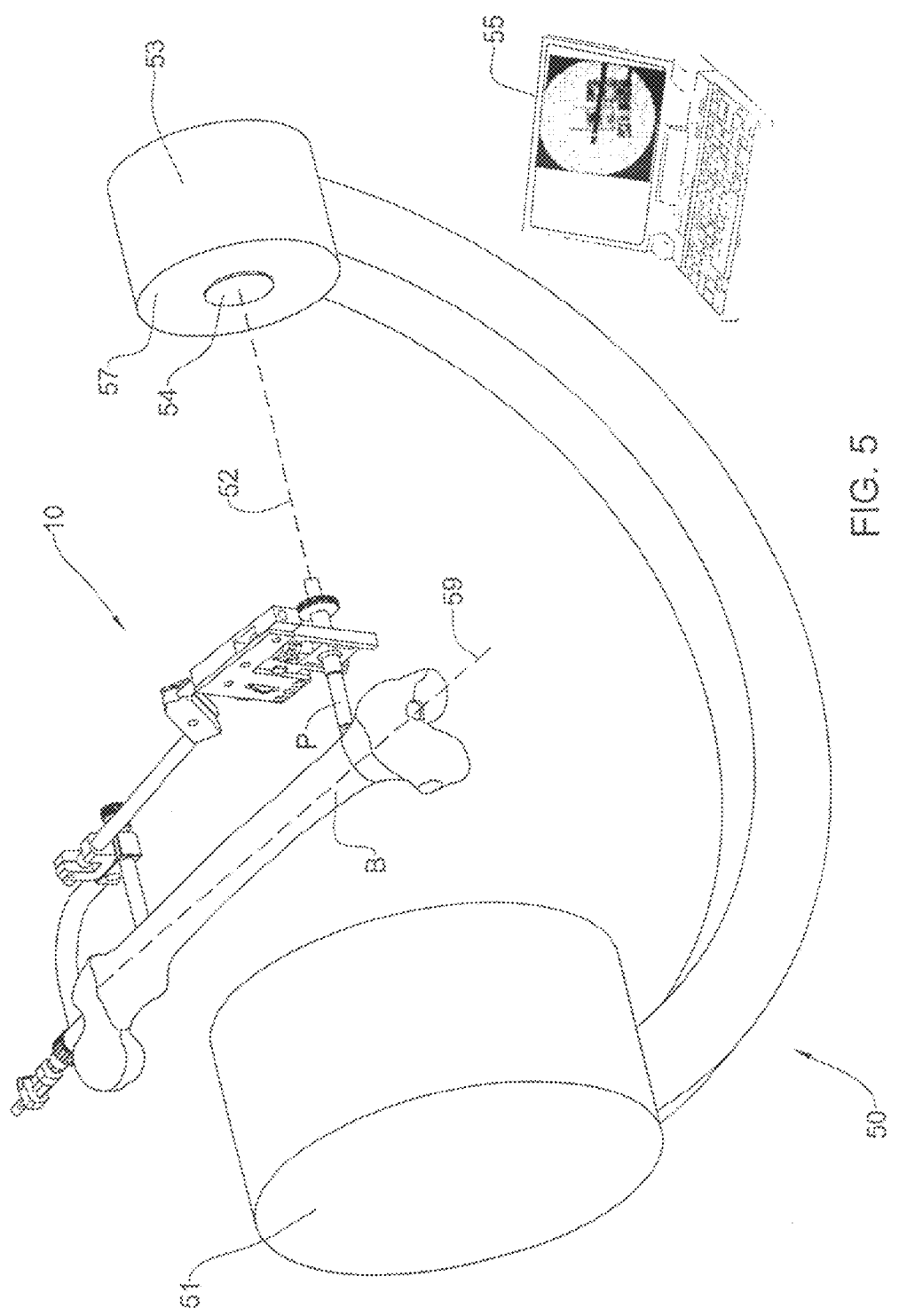
FIG. 5 is a schematic illustration of the system shown in FIG. 1A as used with a C-arm X-ray machine.

FIG. 5 illustrates the system 10 mounted on the bone B and positioned in the radiation field of a C-Arm X-ray machine 50, having an X-ray source 53 and an X-ray receiver 51 having an emitting face 57, to which a mirror 54 may be attached as shown. The bone B has the nail 11 inserted therein (not seen) and the jig 12 is attached to the bone B, as previously described. The C-Arm 50 is rotatable about the longitudinal axis 59 around the bone B, so that X-ray images may be taken by the C-Arm from different angles. There is further provided an image processing software and hardware 55, which may be connected directly or indirectly to the system 10, for processing X-ray images taken by the C-Arm 50.

The use of the system 10 for the determination of the location of the distal hole 13 comprises the following stages:
1. Pre-adjustment of the positioning head 15 prior to the insertion of the nail 11 into the bone B;
2. Insertion of the nail 11 into the bone B and attaching the jig 12
3. Initial adjustment of the C-Arm 50 and calculation of the parameters of initial position of the guiding axis G of the system relative to the hole axis H.
4. Insertion of the viewing optics 81 into the positioning head 15;
5. Insertion of the disposable member 22 into the nail 11 and determination of an entry point at which in future a drilling bit will be located for drilling the bone B;
6. Insertion the alignment pin 41 into the ball joint 17, taking X-ray images and calculation of the parameters of the updated position of the guiding axis G relative to the hole axis H.
7. Moving the ball joint 17 to adjust the position of the guiding axis G based on the updated parameters;
8. Adjusting the C-Arm 50 according to the new position of the ball joint 17 and taking an additional, control X-ray image.

Each of the above stages will now be described in more detail.
1. Pre-Adjustment of the Positioning Head 15 Prior to the Insertion of the Nail 11 into the Bone B The disposable member 22 is inserted into the nail 11 when the nail 11 is still outside the bone, and the position of the laser source 21 therein is adjusted by the locking bosses 25 so that the laser source is aligned with the axis H of the distal hole 13. Since the adjustment is performed when the nail 11 is outside the bone, the distal hole 13 and the laser source aligned therewith are clearly seen. Therefore, activation of the laser is not necessarily needed for the adjustment and it may be activated just for check-up purposes.

The jig 12 is attached to the nail 11 at its proximal end 12a by means of the handle 14 and the universal joint 19b using an aligning conductor (not shown) or by any other appropriate way known in the art. The positioning head 15 is adjusted to align the axis G thereof with the distal hole axis H. The Y axis of the positioning head 15 is made parallel to the axis of the nail, while the G axis is initially made parallel to the Z axis of the jig 12 by setting the ball joint 17 in the pre-defined 90° position. The X-Y plane of the positioning head should be normal to the G axis. After the adjustment of the positioning head 15, the proximal joint 19a, the universal joint 19b, the positioning screws 15a and 15b, and the ball joint 17 are locked and the jig 12 together with the handle 14 is dismantled from the nail 11 and put aside. This pre-adjustment is performed only once, matching the jig set-up to the specific nail chosen for the operation, and allowing relatively large displacements of the positioning head 15 in X or Y directions. Therefore, in further steps only fine adjustment of the ball joint 17 will be needed, which may be achieved by unlocking only the ball joint 17 and by using the positioning screws 15a and 15b. The joints 19a and 19b will remain locked till the end of the procedure.

The purpose of this stage is to bring the positioning head 15 together with the ball joint 17 to a position as accurate as possible relative to the distal hole 13 and to align the axis G with the axis H, thereby facilitating the adjustment thereof after the nail 11 is inserted into the bone B.

2. Insertion of the Nail 11 into the Bone B and Attaching the Jig 12

The nail 11 is inserted into the bone B using traditional techniques, and at the end of the implantation the proximal end of the jig 12a together with the handle 14 is attached to the proximal end of the nail 11a (as shown in FIG. 1A). The jig 12 may be further attached (when improved stability is needed) to the bone B by the proximal support 16 and/or the distal support portion 18 using standard clips and a Schanz screw. When the jig 12 is attached, a penetrating trocar may be inserted through the passage 17a of the ball joint of the positioning head 15, which penetrates the flesh until it touches the bone cortex, in order to expose it and facilitate further steps of the method. The exposure of the bone cortex may be facilitated by other known techniques, e.g. using scalpel to make a small incision.

3. Initial Adjustment of the C-Arm 50 and Calculation of the Parameters of Initial Position of the Guiding Axis G of the System Relative to the Hole Axis H The trocar is pulled out of the passage 17a and replaced with the alignment pin 41. The alignment pin 41 is inserted into the passage 17a, as shown in FIG. 4, whereby its axis P is aligned with the guiding axis G (not shown) of the ball joint 17. The alignment pin 41 is inserted so as to touch the bone at a point T thereon.

With reference to FIG. 5, the laser pointer 45 at the proximal end 41a of the alignment pin 41 is turned on to emit a laser beam 52, which is aligned with the pin axis P, toward the center of the mirror 54 on the emitting face 57 of the X-ray emitter 53 (or the receiving face of the Receiver 51) so as to obtain a beam reflected from the mirror. The coincidence of such reflected beam with the incident laser beam 52 will indicate that the axis of the C-Arm 50 is aligned with the axis of the alignment pin P, and, consequently, with the guiding axis G of the ball joint 17. This coincidence is achieved by locating a spot created by the reflected beam on a plane, e.g. a sheet of paper, positioned close to the laser pointer 45, and adjusting the C-Arm 50 so that the spot is located exactly on the laser pointer 45.

Figure 6A:
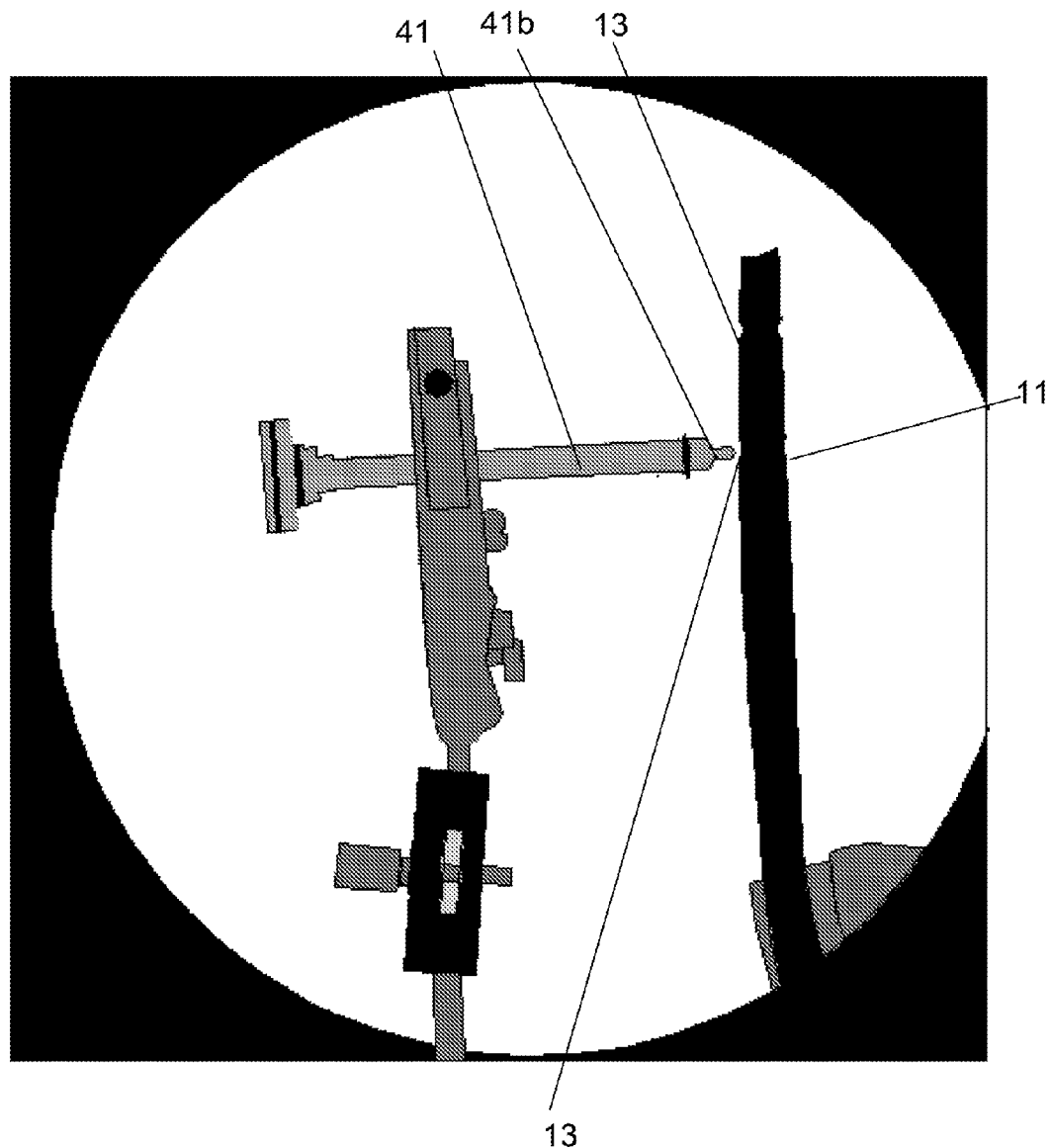
FIGS. 6A and 6B are illustrations of X-ray images of a system built according to one embodiment of the present invention and used as shown in FIG. 5 taken along Y and Z axes, respectively.
Figure 6B:
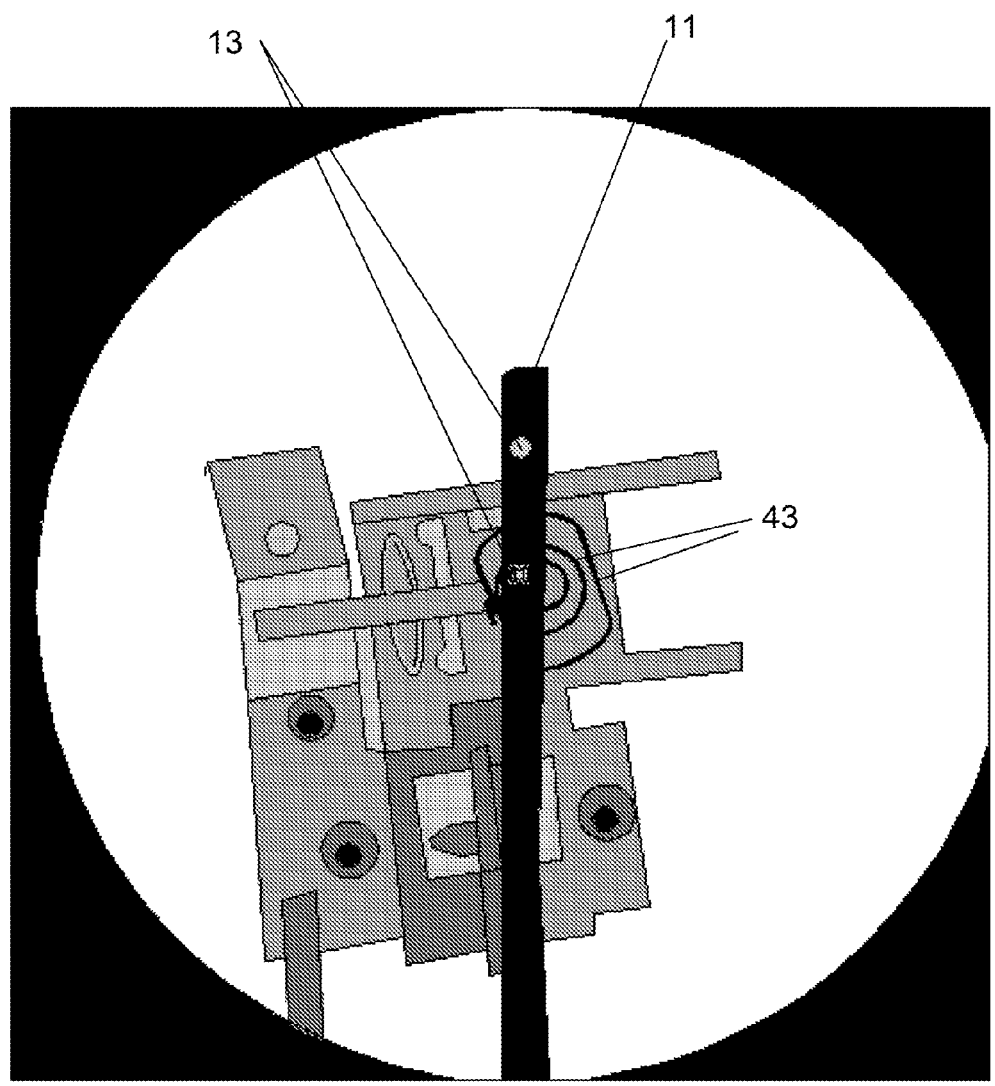

Once the C-Arm 50 is adjusted, two X-ray images of the system with the bone B are taken, examples of which are shown in FIGS. 6A and 6B. The first image is taken along the Y-axis (FIG. 6A) and the second image is taken along the Z-axis (FIG. 6B). Based on these images it is determined whether bending and/or twisting of the nail 11 has been occurred during the implantation of the nail 11 into the bone B. Moreover, since in both of these cases the center of the distal hole 13 and its axis H will not be located at the same place as it was before the implantation, at this stage the location of the center of the distal hole 13 is determined and, in case the twisting occurred, a distance is calculated between the orientation of the hole axis H determined at stage 1 and its new orientation due to the twisting. This distance is designated as $SX_1$ in FIG. 7.

These and other parameters can be determined using the X-ray images as follows:

(a) The center C of the hole 13 is determined visually or using software based on the X-ray image taken along the Z-axis, as shown in FIG. 6B.

(b) The twisting of the nail 11 is determined based on the same X-ray image as used in step (a) above, where non-circularity of the hole 13 indicates to the twisting of the nail. The image further shows the reference marks 43, which appear circular due to the C-arm 50 adjustment. The fact that the marks are not concentric with the hole 13, as shown in FIG. 6B, will indicate the bending of the nail 11.

(c) Based on non-circularity of the distal hole 13 and non-concentricity of the reference marks on the X-ray image taken along the Z-axis with the hole 13, a distance $SX_0$ (not shown) is calculated, which is actually the distance that the guiding axis G of the ball joint should be moved along the X-axis parallel to itself, for the hole axis 13 to meet with the axis G at the bone outer surface. At this stage, the distance $SX_0$ can be only calculated and not actually measured, since the hole 13 is inside the bone and not on the outer surface thereof. The actual measurement of this distance will be performed during further steps.

Figure 7:
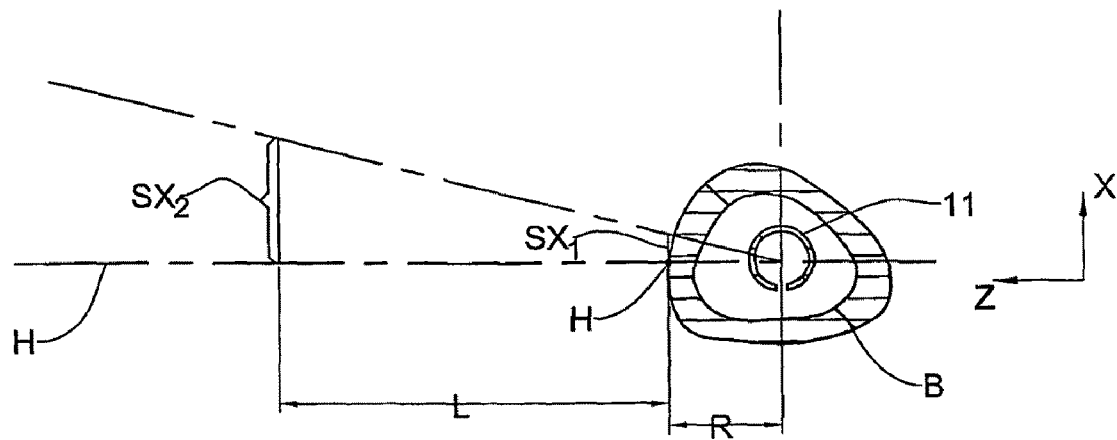
FIG. 7 illustrates a manner in which final position of a guiding axis G of the system shown in FIGS. 1A and 1B, is defined.

The X-ray image taken along the Y-axis (FIG. 6A) allows calculating other distances such as a distance R between the center C of the distal hole 13 and the point T and a distance L—distance between the point T and the center of the ball joint 17, as also schematically shown in FIG. 7

In addition, the size of screws length to be used for fixing the distal end 11b of the nail 11 may be calculated.

It should be noted, that this stage may be optional, and actually may be performed as a part of stage 5 and 6 (see below), which will speed up the operation and reduce the number of X-Ray images taken. The final decision in this respect will be made after sufficient experience with the described procedures is acquired.

4. Insertion of the Viewing Optics 81 into the Positioning Head 15

With reference to FIG. 8A, the alignment pin 41 is replaced with the viewing optics 81 (FIG. 8A, which is inserted into the passage 17, whereby optical axis of the viewing optics is aligned with the guiding axis G.

5. Insertion of the Disposable Member 22 into the Nail 11 and Determination of an Entry Point at which in Future a Drilling Bit Will be Located for Drilling the Bone B The disposable member 22 is inserted into the nail 11 and adjusted as described in stage 1. The laser is then activated and as a result of the laser beam 24 projected though the distal hole 13 and the surrounding tissue of the bone, whereby a spot 26 is created on the outer surface of the bone B, as shown in FIG. 3. The spot 26 is viewed by the viewing optics and the center of the spot is determined visually or by using software, indicating the intersection of the distal hole axis H with the outer surface of the bone B. The center of the spot in fact constitutes an entry point E at which a drilling bit will enter the bone. The viewing optics 81 within the ball joint 17 may be moved manually using the positioning screws 15a and 15b, until it is aligned with the center of the spot 26. The values of this displacement are stored for future use.

This displacement (being a sum of distance $SX_1$ and $SX_0$) is measured and compared to its value calculated in stage 3 based on the X-ray images, so as to assure that the measurement is correct and actual $SX_1$ may be calculated being a result of the nail twisting and not bending. As it may be appreciated from the explanations above, the value of the distance $SX_1$ depends on the extent of the nail distortions which could take place during the insertion process, namely bending and twisting of the nail 11. The results of these distortions may add to or subtract from one another. However, it is important to distinguish between them, and such distinction can be done by using data acquired from X-Ray images and entry point determination. It should be noted, that bending of the nail results in displacement of the hole axis H being parallel to itself, while twisting results in "turning" of the said axis and non-circularity of the hole 13 image in the X-ray images taken along the X-axis. Both movements result in displacement of the laser spot 26 created at the outer surface of the bone.

6. Insertion of the Alignment Pin 41 into the Ball Joint 17, Taking X-Ray Images and Calculation of the Parameters of the Updated Position of the Guiding Axis G Relative to the Hole Axis H The viewing optics 81 is replaced with the alignment pin 41, and it is positioned within the passage 17a as described in stage 3. The disposable member 22 is taken out of the nail 11 and two additional X-ray images are made along the X and Z axes. The distances R, L and $SX_1$ are measured once again based on the X-ray images, to avoid any inaccuracy. The final $SX_1$ distance is then calculated being only the result of twisting (if any) and not of parallel displacement of the hole axis. The distal end of the alignment pin 41b is fixed at the entry point E by any suitable means, even hold by hand.

7. Moving the Ball Joint 17 to Adjust the Position of the Guiding Axis G Based on the Updated Parameters Once the alignment pin 41 is fixed at the entry point E, the adjustment of its axis P (and consequently the guiding axis G) should be made, so that it will be aligned with the axis of the hole H. For this purpose a distance $SX_2$ is calculated (FIG. 7), based on the distances previously calculated. The ball joint 17 is then unlocked, and the positioning screws 15a and 15b are used to move the ball joint 17 with the alignment pin through the distance $SX_2$ along the X-axis (and similarly SY2 along Y axis), while its distal end 41b is held fixed at the entry point E. This displacement is allowed due to the unlocked state of the ball joint 17, in which the axis of the passage in the ball joint 17 may be at different angular positions with respect to the axis of the nail. It should be noted that the displacements shown in FIG. 7 are for the purpose of explanation only, and the value and direction of actual displacement has to be determined in each case.

8. Adjusting the C-Arm 50 According to the New Position of the Ball Joint 17 and Taking an Additional, Control X-Ray Image The C-Arm 50 is adjusted based on the updated position of the alignment pin 41 using the laser pointer 45, similar to the adjustment performed as explained in stage 3. An additional X-ray image is then taken along the Z-axis to assure that the guiding axis G is aligned with the distal hole axis H. If the alignment pin 41 distal end marker is positioned in the center of the hole 13 at the X-Ray image, and the hole 13 image is circular while the circular markers of the alignment pin 41 are concentric with the hole 13—that means that the positioning is made correctly. Any of the above stages may be repeated if the surgeon is not satisfied with the results and he feels that an additional adjustment is needed along both X-axis and Y-axis.

Figure 8B:
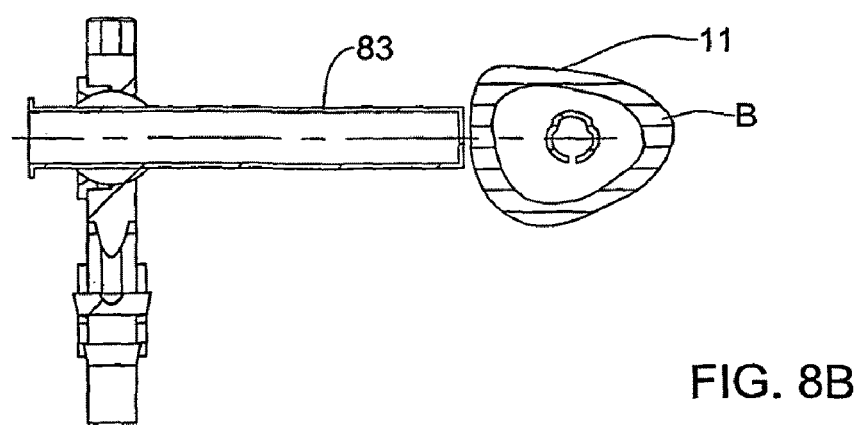

Once the location and the axis of the distal hole 13 are determined and the guiding axis G is aligned with the distal hole axis H, the ball joint 17 is locked, the alignment pin 41 is removed out of the positioning head 15 and replaced with a drilling guide 83 (FIG. 8B) through which a drill bit is inserted and a hole is drilled through the bone B. The nail 11 is then secured in place within the bone by a transversely extending screw or bolt which is inserted through the drilled hole and the Nail distal hole 13.

Since the location of one distal hole 13 is already determined and the ball joint 17 is already adjusted such that its guiding axis G is aligned with the distal hole axis H, a guiding plate (not shown) is affixed to the positioning head 15 and drilling of a second distal hole may be performed. Each of the previously mentioned stages may be repeated for final adjustment of the positioning head 15 with respect to the second distal hole. The second distal hole is then drilled through the bone and the second screw is inserted.

After the distal screws are inserted and affixed, proximal holes, the locations of which are known, are drilled using drill guiding holes usually made in the handle 14 and proximal screws are inserted and affixed.

The invention claimed is:

1. A method for detecting a location of at least one distal hole of an intramedullary nail implanted into a intramedullary canal of a bone, having a proximal end, a distal end and at least one distal hole formed in the nail adjacent said distal end and having a hole axis that is, by means of a system comprising:

a jig having a positioning head with a ball joint having a passage and a guiding axis oriented generally perpendicular to the nail, the ball joint being movable along axes X and Y to bring said guiding axis oriented along Z axis into different spatial positions with respect to said hole axis, being lockable in said positions of the guiding axis and consequently having a locked and unlocked states;

an alignment pin having a pin proximal end, a pin distal end, a portion spaced from its distal end and an alignment pin axis, at least said portion being mountable in said passage of the ball joint so that the alignment pin axis is aligned with the guiding axis and the pin distal end faces towards the bone, said alignment pin further comprises reference marks on its outer surface, visible in X-ray images, in particular said reference marks being coaxial with the pin axis, being disposed at predetermined locations therealong and having predetermined radial dimensions; and a C-arm X-ray machine;

the method comprising:

pre-adiustinq said guidinq axis with the nail axis before the insertion of the nail into the bone, in a way that the guidinq axis is aligned with the hole axis;

fixating said pre-adjusted jig to the proximal end of the nail after insertion of said nail into the bone;

adjusting said C-arm X-ray machine for aligning the axis with said alignment pin axis by means of at least using an X-ray image taken by the C-arm X-ray machine of said alignment pin with said reference marks;

determining a location of a projection of said hole axis on the outer surface of the bone, and the location of the alignment pin axis, using the X-ray image taken by the adjusted C-arm machine, said location defining the level of distortion of said nail and future entry point of the drill bit;

determining the location of said distal hole axis relative to the alignment pin axis by calculating distances and angles desired for aligning the pin axis with the hole axis;

displacing said ball joint while being in its locked state and said portion of the alignment pin received therein, along X and Y axes and positioning the distal end of said pin at said entry point on the outer surface of the bone;

displacing said ball joint while being in its unlocked state and said portion of the alignment pin received therein, along X and Y axes, when the distal end of the pin is fixed at a point on an outer surface of said bone;

locking the ball joint and re-adjusting said C-Arm X-ray machine according to the new position of the alignment pin axis; and taking an additional X-ray image prior to drilling to assure that the alignment pin axis is aligned with the hole axis.

2. The method according to claim 1, wherein said alignment pin has a collimated light source disposed at its proximal end for projecting an alignment beam along said guiding axis in the direction away from the alignment pin.

3. The method according to claim 1, further comprising using said C-arm X-ray machine for taking X-ray images of said bone with said nail, said alignment pin and at least portions of said positioning head.

4. The method according to claim 3, wherein said C-Arm comprises a mirror facing said collimated light source and adapted for use, together with said collimated light source, for aligning the C-Arm's axis with the alignment pin axis.

5. The method according to claim 4, wherein said collimated light source is adapted for projecting said alignment beam along said guiding axis in the direction towards said mirror.

6. The method according to claim 1, further comprising determining a center of said hole projected along the hole axis on the outer surface of said bone.

7. The method according to claim 6, further comprising X-ray image processing hardware and software means for processing X-ray images of the bone with said nail, said alignment pin and at least portions of said positioning head.

8. The method according to claim 6, further comprising inserting a disposable member into said nail and having a nail light source for emitting light along said distal hole axis so as to create an illuminated spot on the outer surface of said bone, said nail light source is of a kind providing collimated light beam along a beam axis and, said member further comprises means for positioning said beam axis along said hole axis.

9. The method according to claim 8, further comprising mounting a viewing optics in said positioning head along said guiding axis for viewing said illuminated spot.

10. A method for detecting a location of at least one distal hole of an intramedullary nail implanted into a intramedullary canal of a bone, having a proximal end, a distal end and at least one distal hole formed in the nail adjacent said distal end and having a hole axis that is, by means of a system comprising:

a jig having a positioning head with a ball joint having a passage and a guiding axis oriented generally perpendicular to the nail, the ball joint being movable along axes X and Y to bring said guiding axis oriented along Z axis into different spatial positions with respect to said hole axis, being lockable in said positions of the guiding axis and consequently having a locked and unlocked states;

an alignment pin having a pin proximal end, a pin distal end, a portion spaced from its distal end and an alignment pin axis, at least said portion being mountable in said passage of the ball joint so that the alignment pin axis is aligned with the guiding axis and the pin distal end faces towards the bone; said pin further comprises reference marks on its outer surface, visible in X-ray images, in particular said reference marks being coaxial with the pin axis, being disposed at predetermined locations therealong and having predetermined radial dimensions; and a C-arm X-ray machine;

the method comprising:

a) pre-adjusting said guiding axis with the nail hole axis before the insertion of the nail into the bone, in a way that the guiding axis is aligned with the hole axis;

b) fixating said pre-adjusted jig to the proximal end of the nail after insertion of the said nail into the bone;

c) adjusting said C-arm X-ray machine for aligning its axis with said alignment pin axis by means of at least using X-ray image taken by the C-arm X-ray machine of said alignment pin with said reference marks;

d) determining a location of a projection of said hole axis on the outer surface of the bone and the location of the alignment pin axis, using X-ray image taken by the adjusted C-arm machine; said location defining the level of distortion of said nail and future entry point of the drill bit;

e) determining the location of said distal hole axis relative to the alignment pin axis by calculating distances and angles desired for aligning the pin axis with the hole axis;

f) displacing said ball joint and said portion of the alignment pin received therein, so as to align the alignment pin axis with the hole axis; and g) re-adjusting said C-Arm X-ray machine according to the new position of the alignment pin axis.

* * * * *